(12) United States Patent
Lakowicz et al.

(10) Patent No.: US 6,472,221 B1
(45) Date of Patent: Oct. 29, 2002

(54) LIFETIME-BASED SENSING OF SODIUM AND POTASSIUM

(75) Inventors: Joseph R. Lakowicz, Ellicott City, MD (US); Henryk Szmacinski, Carmel, IN (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/666,721

(22) Filed: Sep. 20, 2000

Related U.S. Application Data

(63) Continuation of application No. PCT/US99/05980, filed on Mar. 19, 1999.
(60) Provisional application No. 60/111,554, filed on Dec. 9, 1998.

(51) Int. Cl.[7] ................................................. C12Q 1/00
(52) U.S. Cl. ......................................... 436/79; 436/177
(58) Field of Search ............................. 436/73, 79, 172

(56) References Cited

U.S. PATENT DOCUMENTS

| | | | | |
|---|---|---|---|---|
| 5,134,232 A | * | 7/1992 | Tsien et al. | 540/467 |
| 5,624,847 A | * | 4/1997 | Lakowicz et al. | 436/68 |
| 5,759,767 A | * | 6/1998 | Lakowicz et al. | 435/4 |

FOREIGN PATENT DOCUMENTS

| WO | 98/16656 | * | 4/1998 |
|---|---|---|---|

OTHER PUBLICATIONS

A. Minta et al, "Flourescent Indicators forCystolic Sodium" The Journal of BiologicalChemistry, 1989, vol. 264, pp. 19449–19457.*

A. T. Harootunian et al, "Fluorescence RatioImaging of Cystolic Free Na+ in IndividualFibroblasts and Lymphocytes" The Journal ofBiological Chemistry, 1989, vol. 264, pp. 19458–19467.*

H. Satoh et al, "Quantification odIntracellular Free Sodium Ions by Using aNew Fluorescent Indicator, Sodium–BindingBenzofuran Isophthalate in Guinea PigMyocytes" Biochemical and BiophysicalResearch Communications, 1991, vol. 175,pp. 611–616.*

J. R. Lakiwicz et al, "FluorescenceLifetime–Based Sensing of Blood Gases andCations" SPIE, 1992, vol. 1648, pp. 150–163.*

R. Crossley et al, "Synthesis and Propertiesof a Potential Extracellular FluorescentProbe for Potassium" Journal of the ChemicalSociety Perkin Transactions 2, 1994, pp. 1615–1623.*

(List continued on next page.)

*Primary Examiner*—Arlen Soderquist
(74) *Attorney, Agent, or Firm*—Rothwell, Figg, Ernst & Manbeck

(57) ABSTRACT

A system and method of optically measuring $Na^+$ and $K^+$ in a sample such as blood which contains high concentrations $Na^+$ (up to 160 mM) and $K^+$ (up to 6.5 mM) using a photoluminescent probe having intrinsic analyte-induced lifetime changes. Specifically, the use of lifetime-based sensing of $Na^+$ and $K^+$ at the extracellular concentrations present in whole blood or, blood serum. The preferred embodiment uses phase-modulation fluorometry.

14 Claims, 9 Drawing Sheets

OTHER PUBLICATIONS

G. P. Amorino et al, "Intracellular Na+Measurements Using Sodium Green Tetraacetatewith Flow Cytometry" Cytometry, 1995, vol. 21, pp. 248–256.*

H. Szmacinski et al. "Sodium Green as a Potential Probe forIntracellular Sodium Imaging Based on Fluorescence Lifetime" Analytical Biochemistry, 1997, vol. 250, pp. 131–138.*

Enrico Gratton, Resolution of Mixtures of Fluorophores Using Variable–Frequency Phase and Modulation Data, Biophys. J., 1984, pp. 479–486, vol. 46.

R.P. Haugland, Alternative Fluorescence Techniques for Measuring Na+ and K+, Handbook of Fluorescent and Research Chemicals, 1996, p. 575, Molecular Probes, Inc. Eugene, OR.

Haurui He et al., Novel Type of Ion–Selective Fluorosensor Based on the Inner Filter Effect: An Optrode for Potassium, Analytical Chemistry, 1993, pp. 123–127, vol. 65(2).

Gabor Laczko et al., A 10–GHz frequency–domain fluorometer, Rev. Sci. Instrum., 1990, pp. 2331–2337, vol. 61(9), American Institute of Physics.

Joseph R. Lakowicz et al., Analysis of Fluorescence Decay Kinetics from Variable–Frequency Phase Shift and Modulation Data, Biophys. J., 1984, pp. 463–477, vol. 46.

Joseph R. Lakowicz et al., Frequency–Domain Fluorescence Spectroscopy, Topics in Fluorescence Spectroscopy, 1991, pp. 294–334, vol. 1, Plenum Press, NY.

Joseph R. Lakowicz et al., Calcium Imaging Using Fluorescence Lifetimes and Long–Wavelength Probes, Journal of Fluorescence, 1992, pp. 47–62, vol. 2(1), Plenum Printing Corp.

J.N. Roe et al., Optical measurement of aqueous potassium concentration by a hydrophobic indicator in lipid vesicles, Biophysical Chemistry, 1989, pp. 295–302, vol. 33, Elsevier Science Publishers B.V.

J.N. Roe et al., Fibre Optic Sensor for the Detection of Potassium Using Fluorescence Energy Transfer, Analyst, 1990, pp. 353–358, vol. 115.

H. Szmacinski et al., Possibility of simultaneously measuring low and high calcium concentrations using Fura–2 and lifetime–based sensing, Cell Calcium, 1995, pp. 64–75, vol. 18, Pearson Professional Ltd.

Henryk Szmacinski, Fluorescence Lifetime Characterization of Magnesium Probes: Improvement of Mg2+ Dynamic Range and Sensitivity Using Phase–Modulation Fluorometry, Journal of Fluorescence. 1996, pp. 83–95, vol. 6(2), Plenum Publishing Corporation.

Nancy L. Thompson, Fluorescence Correlation Spectroscopy, Topics in Fluorescence Spectroscopy, 1991, pp. 337–355, vol. 1, Plenum Press, NY.

* cited by examiner

SBFO

CD 222

NaCl (———) or KCl (----) (mM)

LIFETIME-BASED SENSING OF SODIUM AND POTASSIUM

CROSS-REFERENCE TO RELATED APPLICATION

The present application is a continuation application of PCT/US99/05980, filed Mar. 19, 1999, which claims the benefit of U.S. Serial No. 60/111,554, filed Dec. 9, 1998.

The development of the present invention was supported by the University of Maryland, Baltimore, Md. and by funding from the National Institutes of Health under contract number NIH RR08119. The United States Government has a non-exclusive, irrevocable, paid-up license to practice or have practiced for or on behalf of the United States the invention herein as provided for by the terms of the above-mentioned contracts awarded by the United States Government.

FIELD OF THE INVENTION

The present invention relates to the field of optically measuring sodium or potassium concentrations in solutions.

BACKGROUND OF THE INVENTION

Measurement of electrolytes in the blood is an important aspect of clinical chemistry. The most common techniques used for measuring electrolytes in aqueous environments are flame photometry or ion selective electrodes (ISE). Both flame photometry and ISE are highly evolved technologies which provide good precision and accuracy over a wide range of concentrations. These methods require good operator skills and meticulous maintenance of equipment for optimal performance. Additionally, these methods require the handling of blood, which is expensive and associated with significant health risks to the operator.

In recent years there has been an increased emphasis on the use of optical probes for clinical chemistry. Optical methods have been developed to monitor blood gases (pH, $pCO_2$ and $pO_2$) in whole blood. Optical techniques can be relatively inexpensive, have excellent signal to noise ratio and because they are virtually instantaneous in their response time they can provide immediate answers for point-of-care testing.

Fluorescence assays have been shown to be approximately three orders of magnitude more sensitive than absorption methods and the fluorescence assays also permit analysis using smaller amounts of probe in the assay solution. Moreover, in contrast to absorption methods, fluorescence probes do not require additional chemical reagents and complex sample manipulation.

At present, most fluorescence assays are based on the change in fluorescence intensity which occurs in response to an analyte. While fluorescence intensity measurements are simple and accurate in the laboratory, these are often inadequate in real world situations. A significant disadvantage of intensity-based sensing is the problem of referencing. The intensity depends on a number of instrumental factors and on the probe concentration. For instance, the intensity for a given sensor can depend on the details of the optical correction efficiency or on the concentration of the fluorophore in the sensor itself. Hence, frequent recalibration is needed for most intensity-based measurements.

A method in which a luminescent ligand is added to a sample to be analyzed in the form of a photoluminescent probe having intrinsic analyte-induced lifetime changes is known in the art. Lifetime measurements are advantageous over intensity measurements because they can be performed in optically dense samples or turbid media and are independent of and/or insensitive to photo bleaching, probe wash out or optical loss. The lifetime changes are measured using known time-resolved or phase-modulation fluorometry methods. A description of the phase modulation fluorometry methods are found in U.S. Pat. No. 5,624,847 ('847 patent) which is incorporated by reference herein in its entirety. The step of adding a luminescent ligand (i.e., probe) to the sample to be analyzed requires matching a particular probe to a particular analyte, so that at least a portion of the sample will be non-covalently bound to the probe resulting in both bound and unbound species of the probe.

While the use of lifetime-based sensing and phase-modulation fluorometry disclosed in the prior art is useful for determining analytes in certain solutes, the problems of quantification associated with other solutions, particularly extracellular ones, were not previously recognized. There has been a clinical need to extend the use of lifetime-based sensing and phase-modulation fluorometry to such solutions.

SUMMARY OF THE INVENTION

One of the problems not previously recognized is the difficulty of measuring alkali metal ions that have similar properties and are difficult to distinguish one in the presence of the other. In blood, the mean concentrations of sodium and potassium are 140 mM and 4.5 mM, respectively. It is difficult to achieve selective detection of $K^+$ in the presence of a 30 fold excess of chemically similar $Na^+$.

Development of a $K^+$ sensor using as ionophore, like valinomycin, based on the inner filter effect (H. He, H. Li, G. Mohr, B. Kovác, T. Werner, and O. S. Wolfbeis, Novel Type of Ion-Selective Fluorosensor Based on the Inner Filter Effect:

An Optrode for Potassium. *Anal. Chem.* 65, 123–127, 1993) or energy transfer (J. N. Roe, F. C. Szoka, and A. S. Verkman, Optical measurement of aqueous potassium concentration by a hydrophobic indicator in lipid vesicles. *Biophys. Chem.* 33, 295–302, 1989; J. N. Roe, F. C. Szoka, and A. S. Verkman, Fibre optic sensor for detection of potassium using fluorescence energy transfer. *Analyst* 115, 353–368, 1990) has been attempted. One difficulty with energy transfer sensing is that the extent of energy transfer strongly depends on acceptor concentration, so that the sensor will require frequent calibration. This problem can potentially be circumvented by using covalently linked donors and acceptors. However, few such sensors have appeared due to the difficulties with chemical synthesis.

The present invention provides a method of optically measuring $Na^+$ or $K^+$ in a sample such as blood, containing concentrations of up to 6.5 mM of $K^+$ and of up to 160 mM of $Na^+$. A photoluminescent ligand probe having intrinsic sodium- or potassium-induced lifetime changes is added to the sample to be analyzed. The probe is non-covalently bound to the ionic solute of either sodium or potassium to form a $Na^+$-bound or $K^+$-bound probe species wherein bound and unbound species of the probe exist in the sample and the probe has intrinsic $Na^+$-induced or $K^+$-induced lifetime changes. The sample is excited with radiation and the resulting emission beams from the bound and unbound species are detected. The apparent luminescence lifetime of the emission is calculated to determine concentration of either $Na^+$ or $K^+$ in the sample. Because of the similar chemical properties of $Na^+$ and $K^+$, probes are utilized such that the presence of high levels of $Na^+$ allows the measurement of $K^+$ and the presence of $K^+$ allows the measurements of $Na^+$.

DETAILED DESCRIPTION OF THE PREFERRED EMBODIMENTS

In the current invention, a fluorescent method for sensing $Na^+$ and $K^+$ at the concentrations found in whole blood is presented. Probes which display useful changes in luminescence lifetime in response to the sodium and potassium in cation concentrations in the ranges found in blood are identified.

Figure 1A:
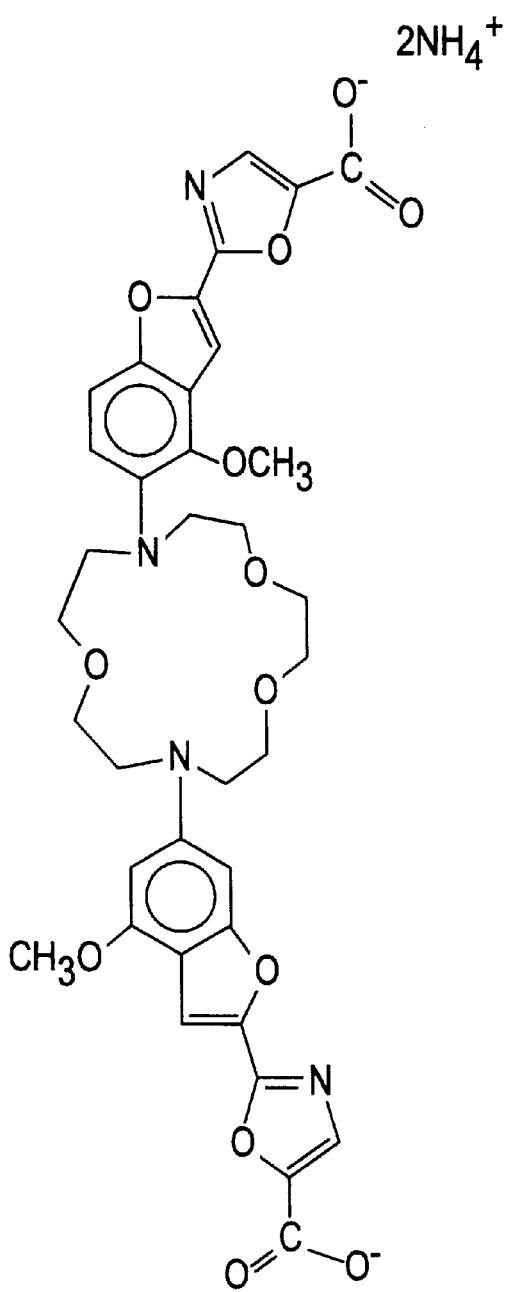
FIG. 1, chemical structures of SBFO and CD 222.
Figure 1B:
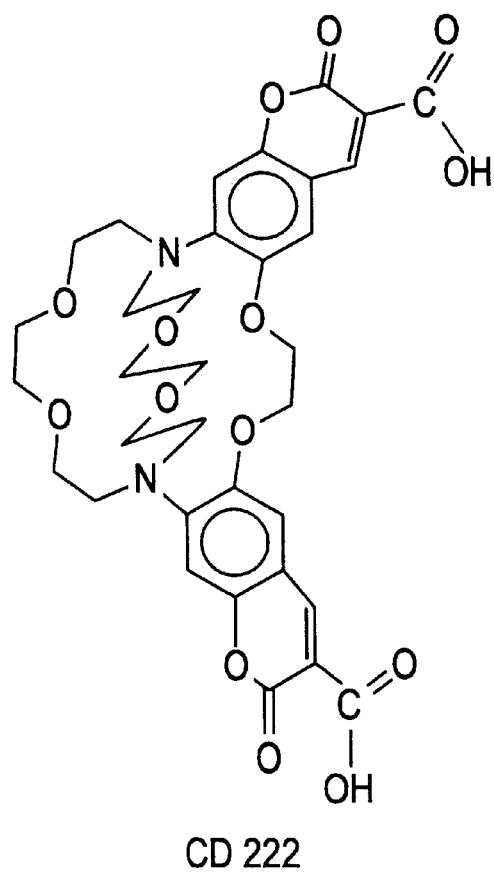

The chemical structures of SBFO and CD 222 are shown in FIG. 1. Absorption spectra were measured using a HP 8453 spectrometer. Steady-state intensity measurements were performed using an Aminco-Bowman AB2 spectrofluorometer. Fluorescence intensity decays were measured with a frequency-domain instrumentation previously described in G. Laczko, I. Gryczynski, Z. Gryczynski, W. Wiczk, H. Malak, and J. R. Lakowicz, 10-GHz frequency-domain fluorometer. *Rev. Sci. Instrum.* 61(9), 2331–2337, 1990, and J. R. Lakowicz and I. Gryczynski, Frequency-Domain Fluorescence Spectroscopy. In *Topics in Fluorescence Spectroscopy*, Vol. 1 : *Techniques* (J. R. Lakowicz, ed.), Plenum Press, New York, 1991, pp. 293–355. The excitation light was the cavity dumped and frequency-doubled output of pyridine 2 dye laser (Coherent, Inc.) With the wavelength tunable from 343 to 385 nm. Longer excitation wavelengths (400 nm) were obtained from frequency-doubled output of the Ti:sapphire laser (Spectra Physics, Inc.). The emission was observed through a long wavepass filter which transmitted the probe emission and blocked scattered excitation light.

Cation-dependent intensities, phase angles and modulations for SBFO and CD 222 were measured at several excitation wavelengths because both probes display shifts in their absorption spectra upon cation binding. The samples were freshly prepared before measurements in the buffers, 5 mM Hepes (pH 7.2) for SBFO, and 30 mM Tris (pH 7.25) for CD 222. The ionic strength of the samples started from 100 mM. The buffers contained 100 mM of the tetramethylammonium chloride, TMA(Cl). The measurements were carried out at room temperature of 22° C.

The frequency-domain data were used to determine the intensity decay law using the multi-exponential model (J. R. Lakowicz, E. Gratton, G. Laczko, H. Cherek, and M. Limkeman, Analysis of Fluorescence Decay Kinetics from Variable-Frequency Phase Shift and Modulation Data, *Biophys. J.* 46, 463–477, 1984; E. Gratton, J. R. Lakowicz, B. Maliwal, H. Cherek, G. Laczko and M. Limkeman, Resolution of Mixtures of Fluorophores Using Variable-Frequency Phase and Modulation Data, *Biophys. J.* 46, 479–486, 1984)

$$I(t) = \sum_{i=1}^{n} \alpha_i e^{-t/\tau_i}, \qquad (1)$$

where $\alpha_i$ are the preexponential factors (amplitudes), $\tau_i$ are the decay times, and n the number of exponential components. To eliminate the effects of Brownian rotation magic angle conditions were used for the intensity decay measurements. The mean decay time ($\bar{\tau}$) and fractional intensities $f_i$ of each component are given by:

$$\bar{\tau} = \sum_i \alpha_i \tau_i^2 \Big/ \sum_j \alpha_j \tau_j = \sum_i f_i \tau_i \qquad (2)$$

$$f_i = \alpha_i \tau_i \Big/ \sum_j \alpha_j \tau_j. \qquad (3)$$

The intensity decays of CD 222 were also fitted to a global model in which the decay times were assumed to be independent of the $Na^+$ or $K^+$ concentration, but the amplitudes of decay times variable to reflect changes in the fractional amounts of each species for various concentrations of $Na^+$ or $K^+$. Such analyses have been described previously for calcium (J. R. Lakowicz, H. Szmacinski, and M. L. Johnson, Calcium Imaging Using Fluorescence Lifetimes and Long-Wavelength Probes. *J. Fluoresc.* 2, 47–62, 1992; H. Szmacinski and J. R. Lakowicz, Possibility of simultaneous measuring low and high calcium concentration using Fura-2 and lifetime-based method. *Cell Calcium* 18, 64–75, 1995) and magnesium probes (H. Szmacinski and J. R. Lakowicz, Fluorescence Lifetime Characterization of Magnesium Probes. Improvement of $Mg^{2+}$ Dynamic Range and Sensitivity Using Phase-Modulation Fluorometry , *J. Fluoresc.* 6(2), 83–95, 1996).

The apparent dissociation constants ($K_D^X$) were calculated with the assumption that the stoichiometry of binding is 1:1, $$K_D^X = \frac{X_{max} - X}{X - X_{min}} [M^+] \qquad (4)$$

where [$M^+$] is the ion concentration and X indicates the measured (or calculated) ion-dependent parameter. The e apparent dissociation constant is the parameter linking the fluorescence observable to the ion concentrations. It should be noted that only the ion-dependent intensities yield a true dissociation constant reflecting the equilibrium between free and ion-bound forms of probe. The dissociation constants calculated from the ion-dependent time-resolved data (phase angle, modulation or mean decay time) will usually result in higher or lower values than the true value because time-dependent parameters are not proportional to the concentration of the free or ion-bound forms (H. Szmacinski and J. R. Lakowicz, Lifetime-Based Sensing in *Topics in Fluorescence Spectroscopy*, Vol. 4: *Probe Design and Chemical Sensing* (J. R. Lakowicz, ed.), Plenum Press, New York, 1994, pp.295–334). Also, the titration curves from ion-dependent excitation intensity ratios result with apparent dissociation constants which values depend on the choice of excitation wavelengths (H. Szmacinski and J. R. Lakowicz, Lifetime-Based Sensing in *Topics in Fluorescence Spectroscopy*, Vol. 4: *Probe Design and Chemical Sensing* (J. R. Lakowicz, ed.), Plenum Press, New York, 1994, pp.295–334). For purposes of chemical sensing, the apparent dissociation constant is the more important parameter because this value defines the useful range of ion concentrations which can be measured using a particular spectral observable. The concentration range over which a probe produces an observable response with a chosen parameter is approximately from $0.1 K_D^X$ to $10 K_D^X$.

Measuring Sodium Ion Concentration

Figure 2:
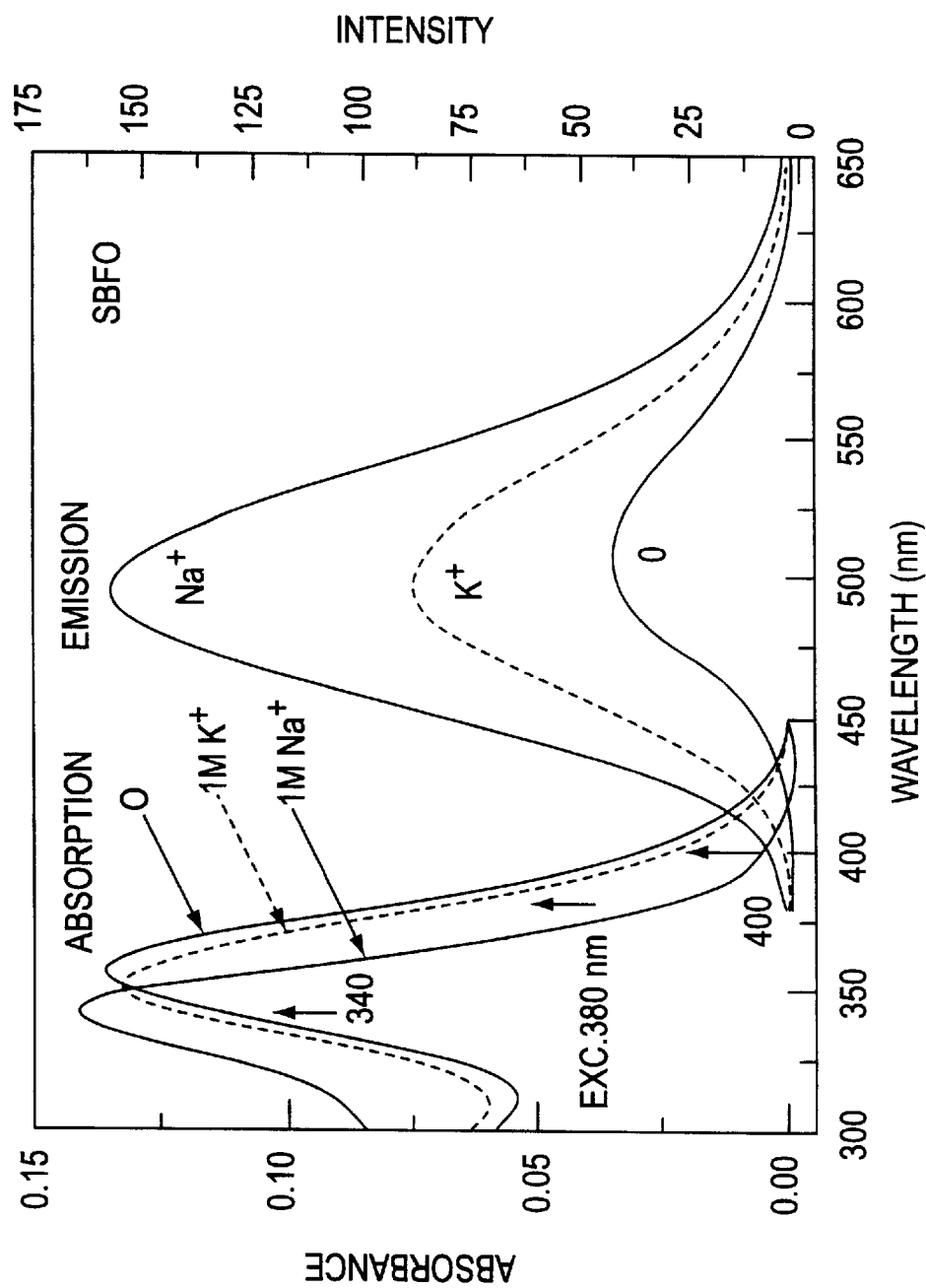
FIG. 2, absorption and emission spectra of SBFO.
Figure 3A:
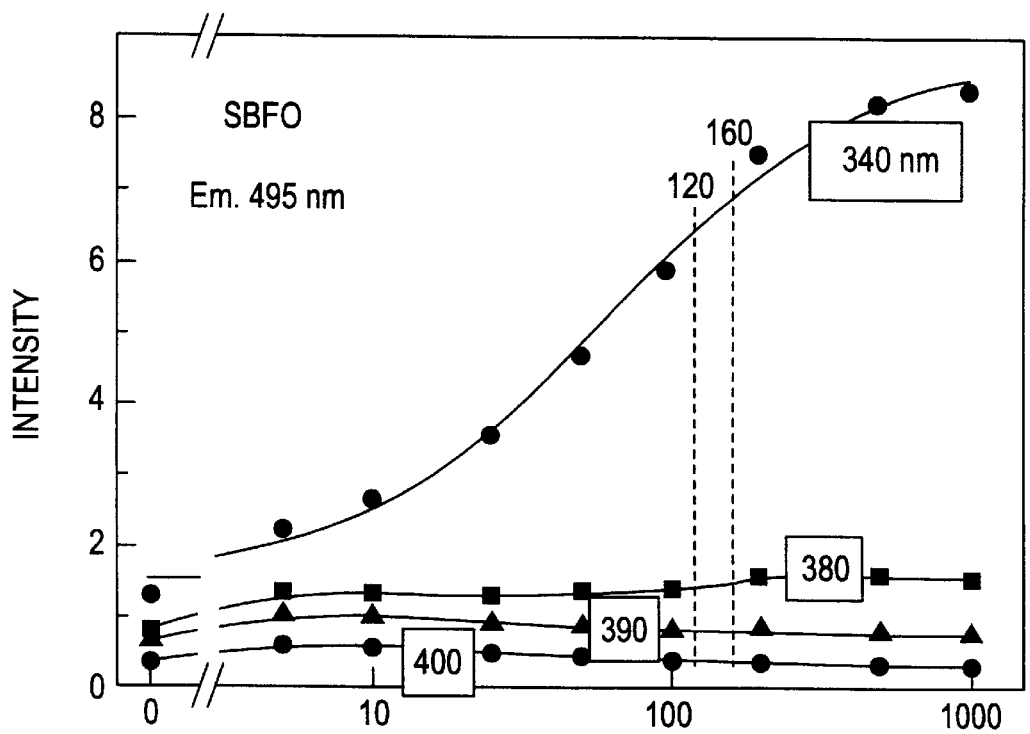
FIG. 3, sodium-dependent fluorescence intensity of SBFO at various excitation wavelengths (top) and excitation intensity ratios (for excitation wavelengths see FIG. 2). Dashed vertical lines illustrate critical concentrations of sodium in the blood.
Figure 3B:
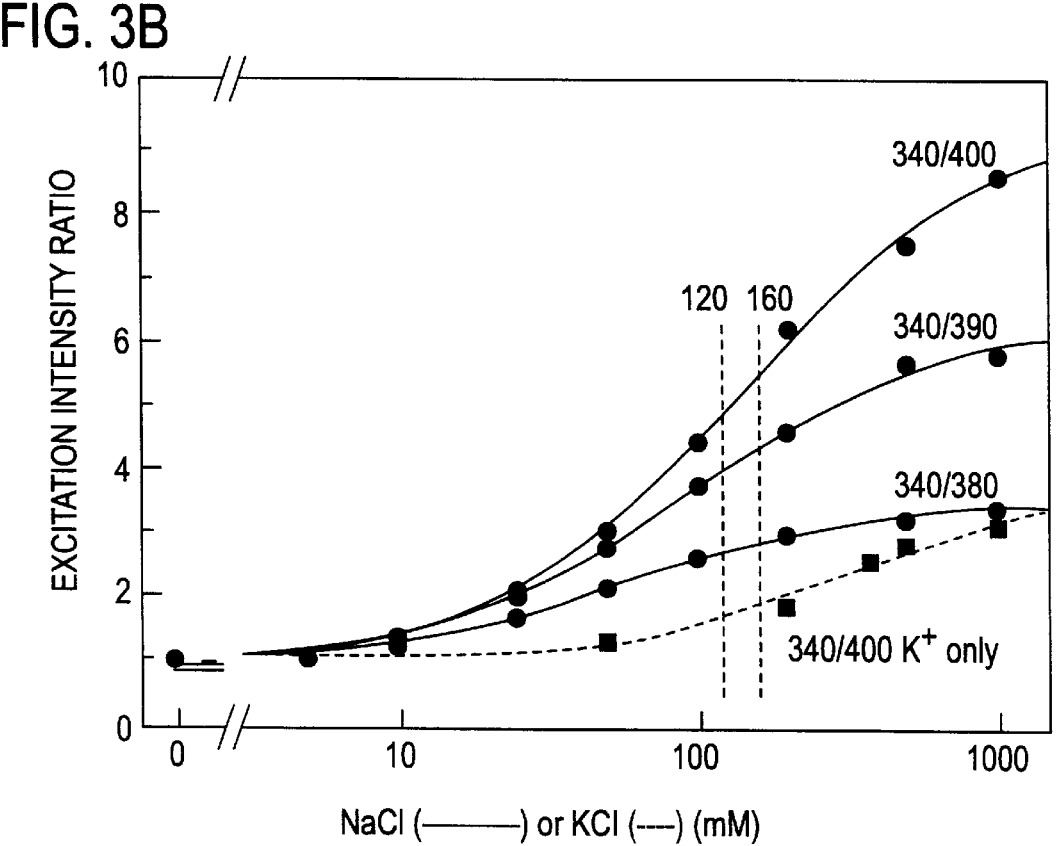

Sodium measurements based on intensities or intensity ratios of sodium binding benzofuran oxazole ("SBFO") are not feasible for measuring the $Na^+$ concentrations present in whole blood. While the presence of $Na^+$ concentrations below 100 mM has essentially no affect on intensity ratios of SBFO, in the most critical range of sodium concentration in the blood, (120 to 160 mM), only a small part of sodium-sensitive range is displayed by SBFO. Measurements of the concentration tolerance of ±3 mM requires intensity measurements with an accuracy of 0.6% and intensity ratio with an accuracy of 0.9%. Such accuracy requirements are difficult to fulfill, particularly using one excitation wavelength. Using a single excitation wavelength, sodium measurements would require strict control of excitation drifts and probe concentration. The limited accuracy of sodium measurements in the range of from 100 to 200 mM with SBFO using intensity ratios has previously been reported (A. T. Harootunian, J. P. Y. Kao, B. K. Eckert, and R. Y. Tsien, Fluorescence ratio imaging of Cytosolic Free $Na^+$ in Individual Fibroblasts and Lymphocytes. *J. Biol. Chem.* 264, 19458–19467, 1989.) Consequently, sodium measurements based on intensities or intensity ratios of SBFO do not seem feasible for the sodium concentration present in whole blood. Further, the absorption spectral changes induced by $K^+$ [FIG. 2] would lead one away from using SBFO as an indicator of $Na^+$ in blood.

Figure 4:
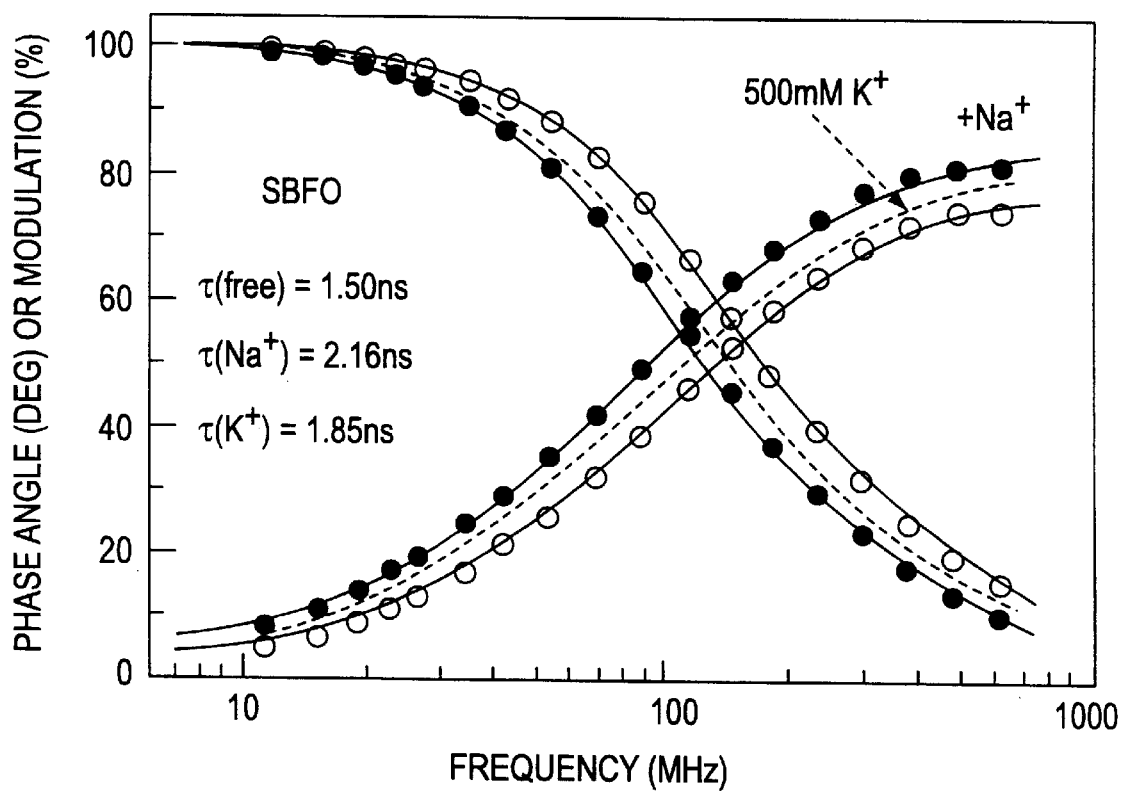
FIG. 4, frequency-domain intensity decays of SBFO.

Unexpected results were obtained when SBFO was used for lifetime-based sensing of sodium in blood. The lifetime of SBFO was determined from the frequency-domain data FIG. 4. The mean lifetime increased from 1.50 ns for the sodium-free form to 2.16 ns for the sodium bound form. The mean lifetime of SBFO was 1.85 ns in the presence of 500 mM of potassium. Table 1 shows the intensity decays of sodium and potassium probes.

TABLE 1

Intensity Decays of Sodium and Potassium Probes

| Probe | Cation (mM) | Decay time (ns) | | | Fractional Intensity | | | $\bar{\tau}$(ns) |
|---|---|---|---|---|---|---|---|---|
| | | $\tau_1$ | $\tau_2$ | $\tau_3$ | $f_1$ | $f_2$ | $f_3$ | |
| SBFO | free | <0.03>[a] | 1.52 | — | 0.016 | 0.986 | — | 1.5 |
| | $Na^+$(1000) | 2.16 | — | — | 1 | — | — | 2.16 |
| | $K^+$(1000) | 0.31 | 1.88 | — | 0.02 | 0.98 | — | 1.85 |
| CD 222 | free | 0.04 | 0.15 | 0.82 | 0.424 | 0.481 | 0.1 | 0.17 |
| | $K^+$(50) | 0.04 | 0.15 | 0.82 | 0.014 | 0.147 | 0.839 | 0.71 |
| | $Na^+$(100) | 0.05 | 0.18 | 1.39 | 0.24 | 0.672 | 0.09 | 0.26 |

[a] The angular brackets indicate this value was held constant in the least square analysis.

As indicated in Table 1, intensity decays of SBFO were almost a single exponential. The dominant cause of sodium-dependent lifetime of SBFO appears to be a minor component with a short lifetime near 30 ps. The major component, with fractional intensity higher than 0.98 increased progressively from 1.52 to 2.16 ns with increasing sodium concentration. Intensity decay changes with SBFO resulted in useful changes in phase angle and modulation, an approximately 11° change in phase and an 11% change in modulation. These changes could be observed from 50–200 MHZ.

Figure 5A:
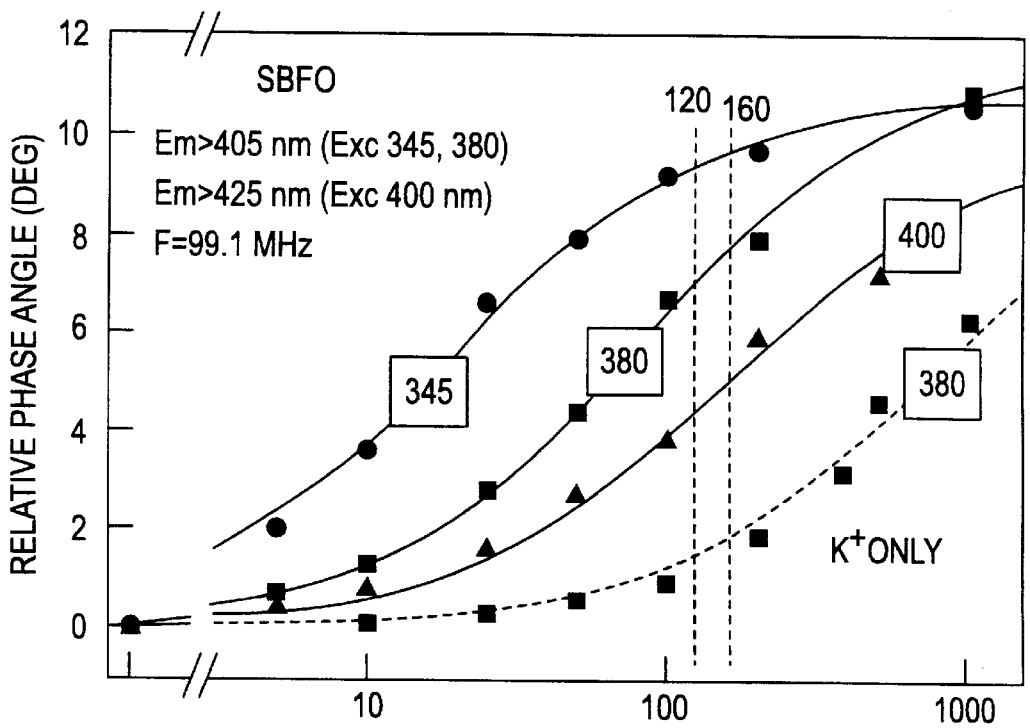
FIG. 5, sodium-dependant phase angles (top) and modulations (bottom) of SBFO at several excitation wavelengths.
Figure 5B:
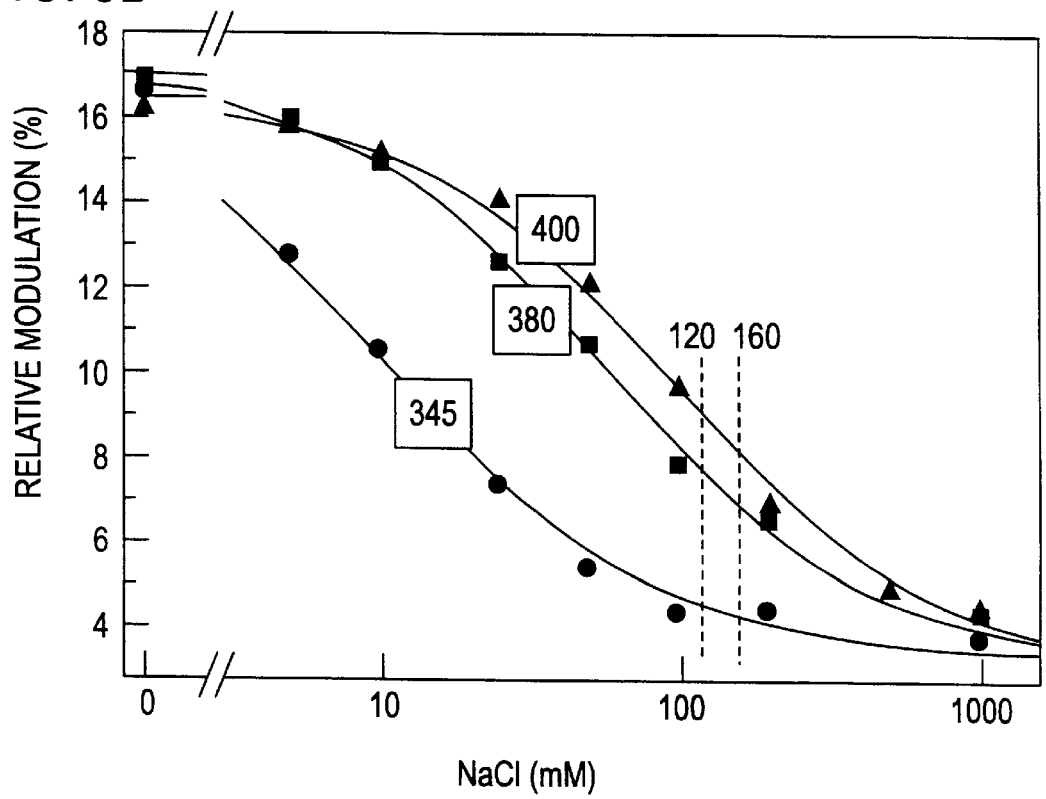

Sodium concentrations can be determined from the phase and modulation values measured at a single light modulation frequency (FIG. 5). The $Na^+$-sensitive range can be adjusted by the choice of the excitation wavelength. For example, the apparent dissociation constants calculated from the phase angle using equation (4), where the X is replaced by the phase angle, are 18.5 mM (345 nm), 81 mM (380 nm), and 154 mM (400 nm). The $Na^+$-sensitive range using modulation is shifted toward lower $Na^+$ concentrations (FIG. 5, bottom), which is usually observed with phase-modulation sensing (H. Szmacinski and J. R. Lakowicz, Lifetime-Based Sensing in *Topics in Fluorescence Spectroscopy*, Vol. 4: *Probe Design and Chemical Sensing* (J. R. Lakowicz, ed.), Plenum Press, New York, 1994, pp.295–334). The respective values of $K_D^{app}$ from the modulation data (FIG. 5, bottom) are 10 mM (345 nm), 49 mM (380 nm), and 157 mM (400 nm). The best $Na^+$ sensitivity for the narrow clinical range of $Na^+$ concentrations (dashed lines) can be obtained for excitation wavelengths from 380–400 nm. The needed accuracy of ±3 mM $Na^+$ requires measurements of phase angle and modulation with an accuracy of 0.06 degrees and 0.09% (at 380 nm excitation). Such accuracy may be achievable with a dedicated single modulation frequency instrument using present optoelectronic technology. For instance, commercially available phase-modulation instruments with a wide range of modulation frequencies provide measurements with an accuracy of 0.1–0.2 degrees and 0.3–0.5% for phase angle and modulation, respectively.

Measuring Potassium Ion Concentration

Figure 6:
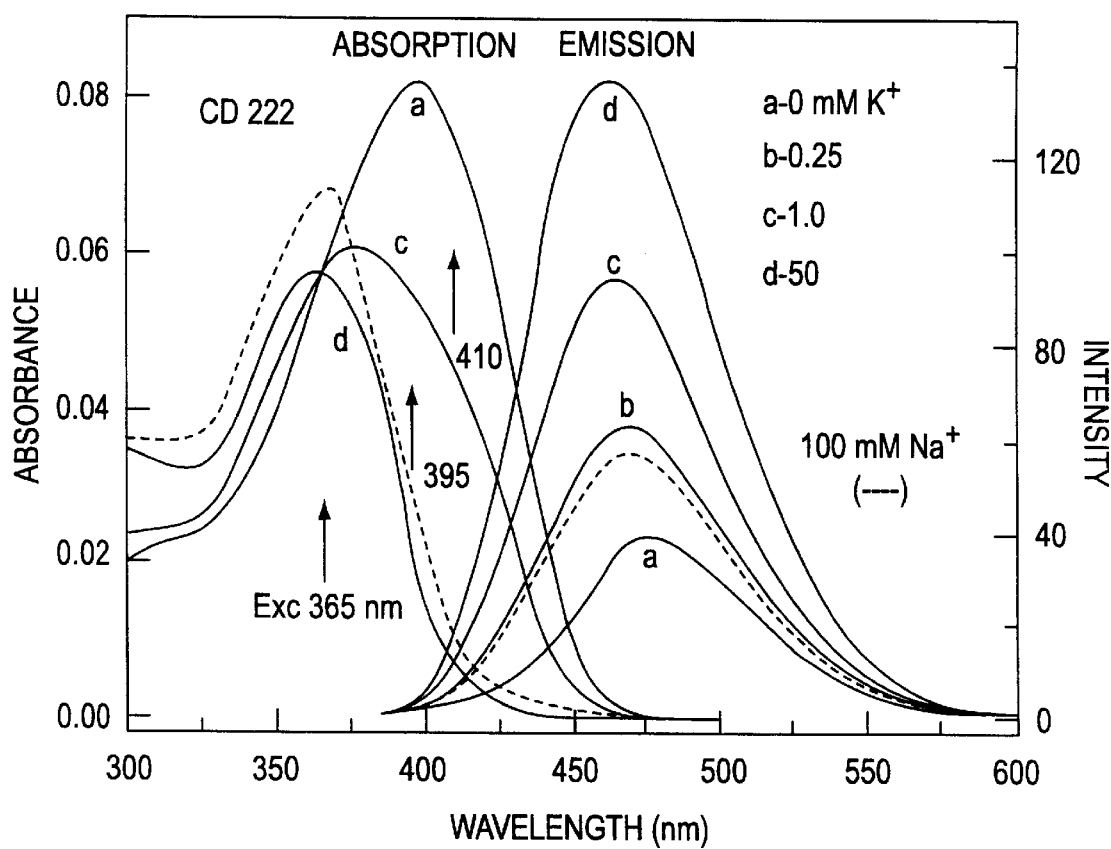
FIG. 6, absorption and emission spectra of CD222 at various $K^+$ concentrations. Emission spectra were taken for 365 nm excitation. CD222 concentration was at 2.7 $\mu$M. Respective spectra of CD222 in presence of 100 mM of sodium are presented by dashed lines.

Absorption and emission spectra of CD 222 are shown in FIG. 6. This probe can be excited at longer wavelengths than PBFI and displays a much larger shift in its absorption spectrum than PBFI. The absorption spectrum displays a 30 nm blue shift upon binding either of $K^+$ or $Na^+$ (dashed line) with a decreasing extinction coefficient above 350 nm. The emission spectra show a minor blue shift on cation binding. The quantum yield of CD 222 fluorescence increases 3.7-fold for the $K^+$-bound form and only 1.4-fold for the $Na^+$-bound form.

The $K_D$ of CD 222 for $K^+$ determined from the intensity is 0.8 mM in the absence of $Na^+$. This value is in close agreement with reported values of 1.0 (R. Crossley, Z. Goolamali, and P. G. Sammes, Synthesis and Properties of a Potential Extracellular Fluorescent Probe for Potassium. *J. Chem Soc. Perkin Trans.* 2, 1615–1623, 1994) and 0.9 mM (R.P. Haugland, Handbook of Fluorescent and Research Chemicals, Molecular Probes, Inc. Eugene, Oreg., 1996, pp 575). FIG. 6 shows that using a CD 222 probe, 100 mM of sodium induces a shift in the absorption spectrum comparable to that found for potassium. This indicates that sodium interferes with the measurement of potassium when performed using absorption, absorption ratio, or excitation intensity ratio measurements, and would lead one away from the use of CD 222 probe to measure potassium in blood.

Figure 7A:
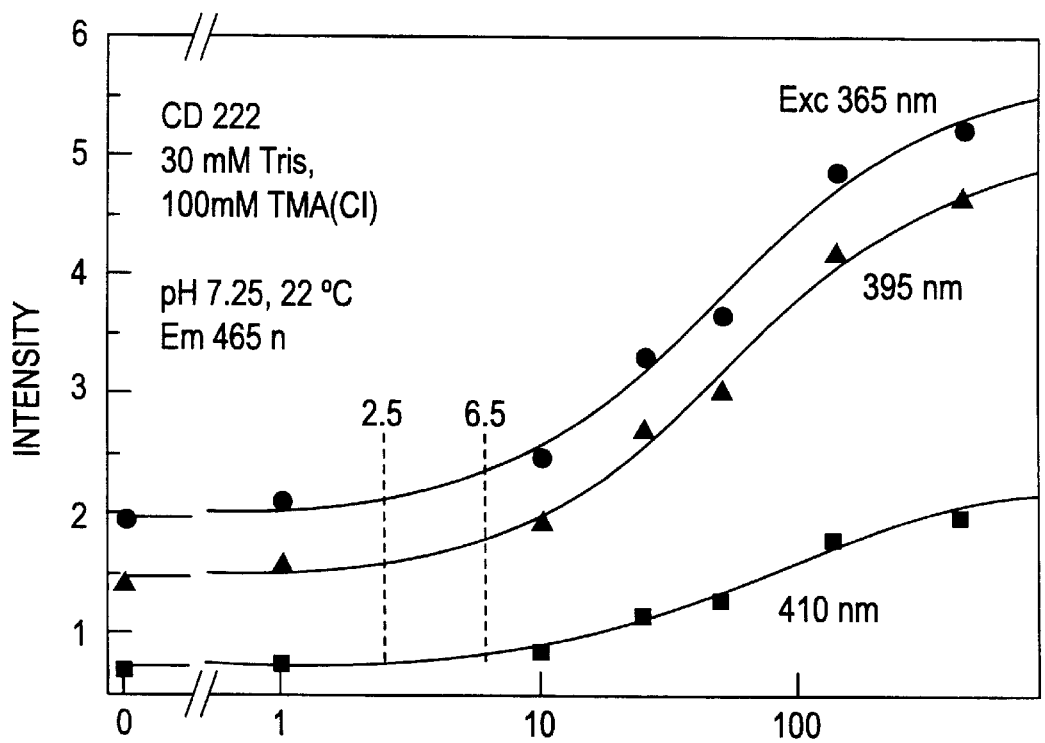
FIG. 7, $K^+$-dependent fluorescence intensity of CD222 in the presence of 135 mM of sodium at various excitation wavelengths and respective excitation intensity ratios (lower panel—dashed vertical lines illustrate critical concentration of potassium in blood).
Figure 7B:
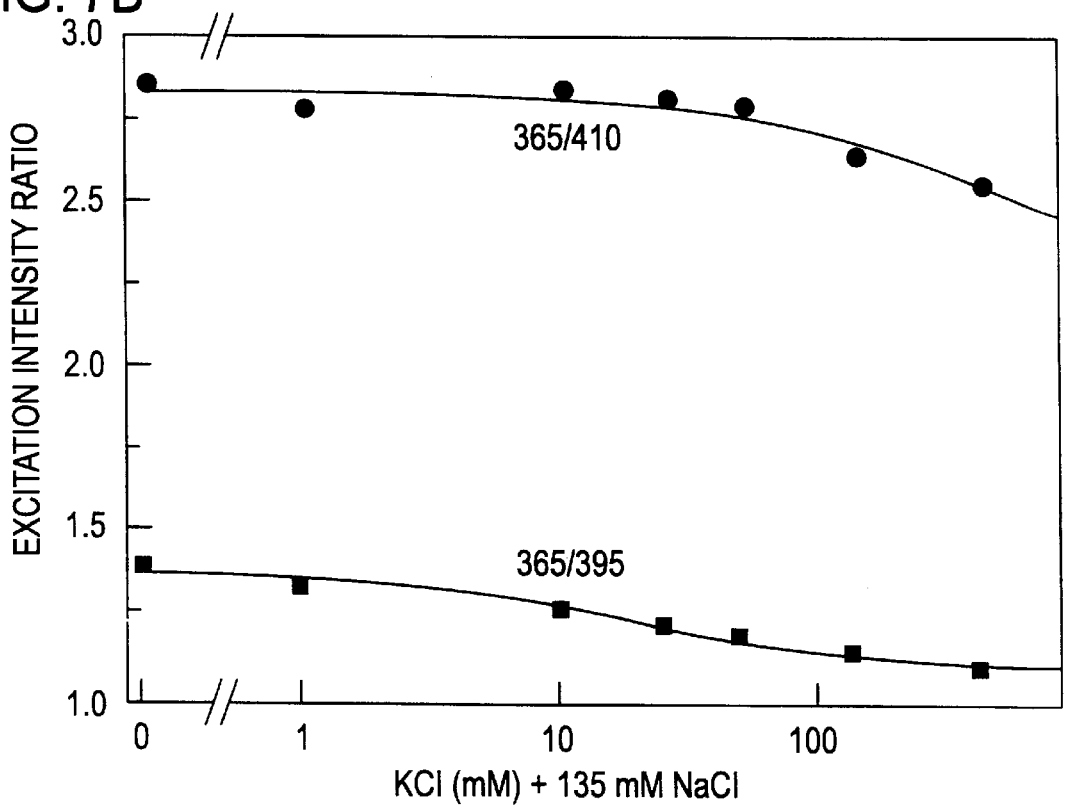

FIG. 7 (top) shows the $K^+$-dependent intensities of CD 222 at various excitation wavelengths in the presence of 135 mM $Na^+$. This concentration of $Na^+$ was used to mimic that found in whole blood. For excitation wavelengths from 365–395 nm the intensities of CD 222 display a good sensitivity to the $K^+$, but above the desired of 2.5–6.5 mM range. This is because the binding constant for $K^+$ (KD=0.8 mM) is strongly affected by $Na^+$, increasing it to 54 mM for the average value from the data for 365 and 395 nm excitation. The respective intensity ratios in the presence of 135 mM $Na^+$ (FIG. 7, bottom) display no sensitivity to $K^+$ concentration for 365/410 and a modest sensitivity for 365/395 ratio in the range up to 10 mM. These results indicate that intensity-based and wavelength-ratiometric sensing of $K^+$ in the blood are not promising using the probe CD 222. Measurements with a concentration tolerance of ±0.2 mM will require intensity measurements (excitation at 365 nm) with an accuracy of about 0.7%. Such an accuracy is usually difficult to obtain in a well controlled cuvette measurements, and not likely to be obtainable in a turbid and colored sample like blood.

Figure 8A:
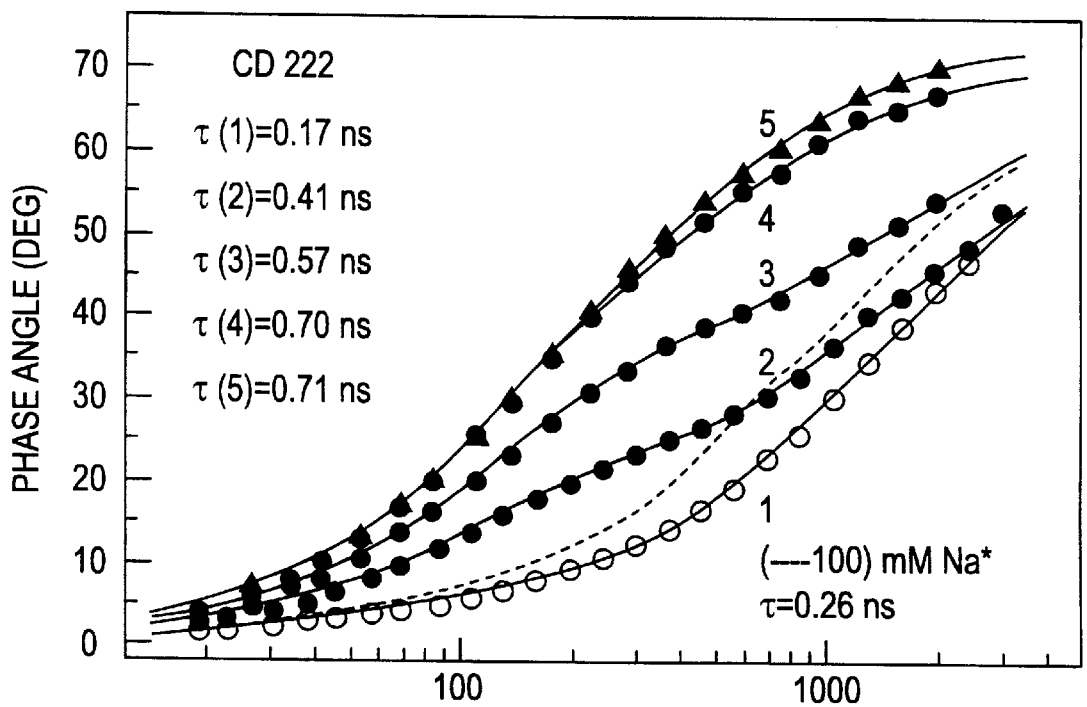
FIG. 8, frequency-domain intensity decays of CD222 for various $K^+$ concentrations. Dashed lines represent intensity decay at the presence of 100 mM of sodium. Excitation wavelength was 380 nM and the emission above 440 nM.
Figure 8B:
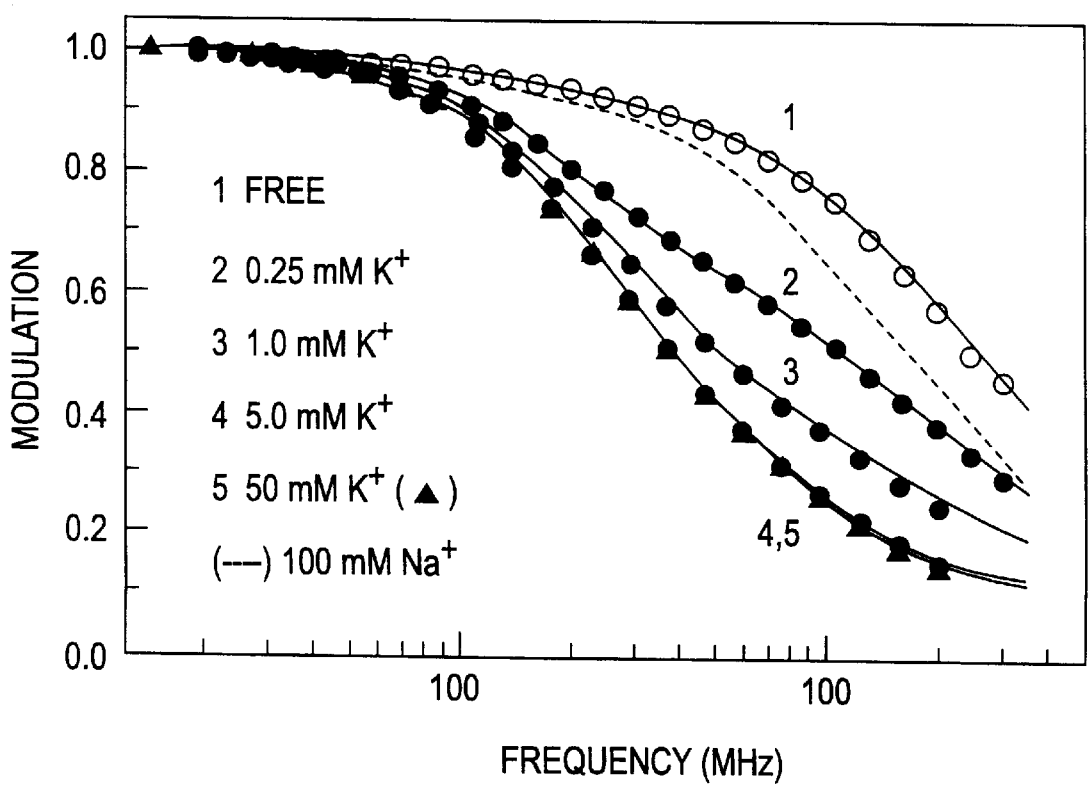

Unexpected results were obtained, however, using the CD 222 probe with lifetime-based sensing. The frequency-domain intensity data of CD 222 was measured with various concentrations of $K^+$ and $Na^+$ (FIG. 8). Global analysis of the intensity decays of CD 222 resulted in three decay times, 0.04, 0.15, and 0.82 ns (Table I). The mean lifetime of CD 222 increased from 0.17 ns for the free form to 0.71 ns for the $K^+$-bound form. In the presence of 100 mM $Na^+$, the mean lifetime is 0.26 ns. Hence, the increase in mean lifetime due to the binding of $Na^+$ to CD 222 is much smaller than the increase in lifetime due to $K^+$. This result suggests the possibility using CD 222 to measure $K^+$ in the presence of high concentrations of $Na^+$. Measurements of potassium in blood can be accomplished with lifetime-based sensing, because the $Na^+$ induced lifetime changes in CD 222 are much less than that induced by $K^+$.

Figure 9A:
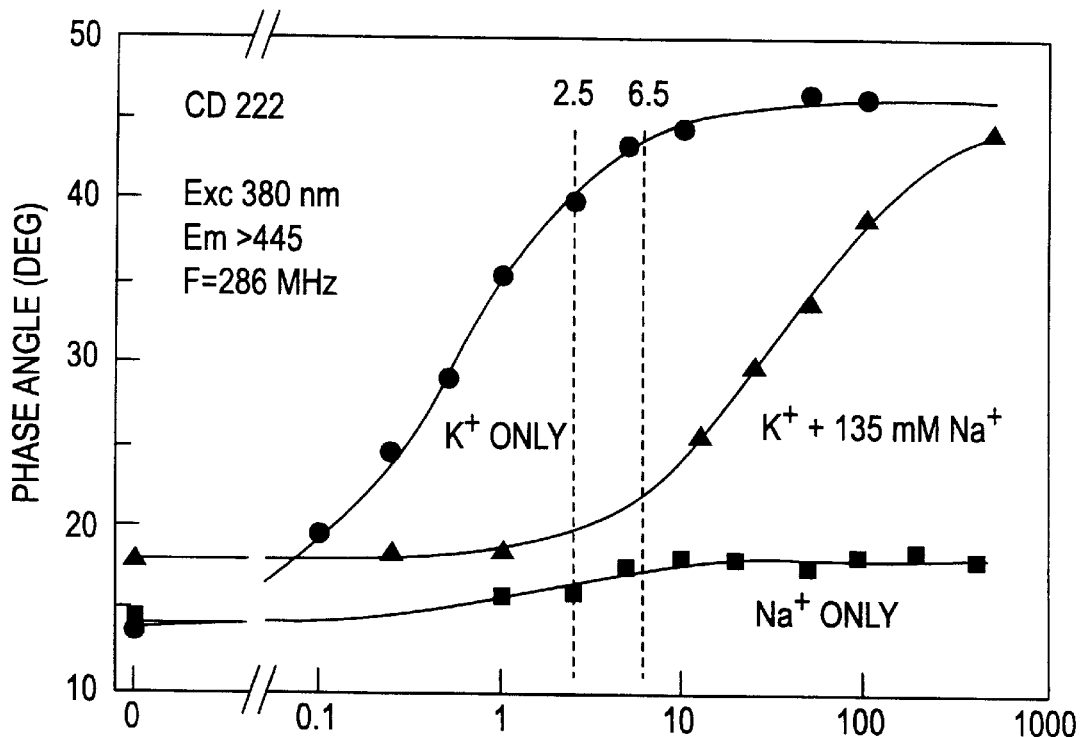
FIG. 9, cation-dependent phase angles (top) and modulations (bottom) of CD222 for various solution compositions.
Figure 9B:
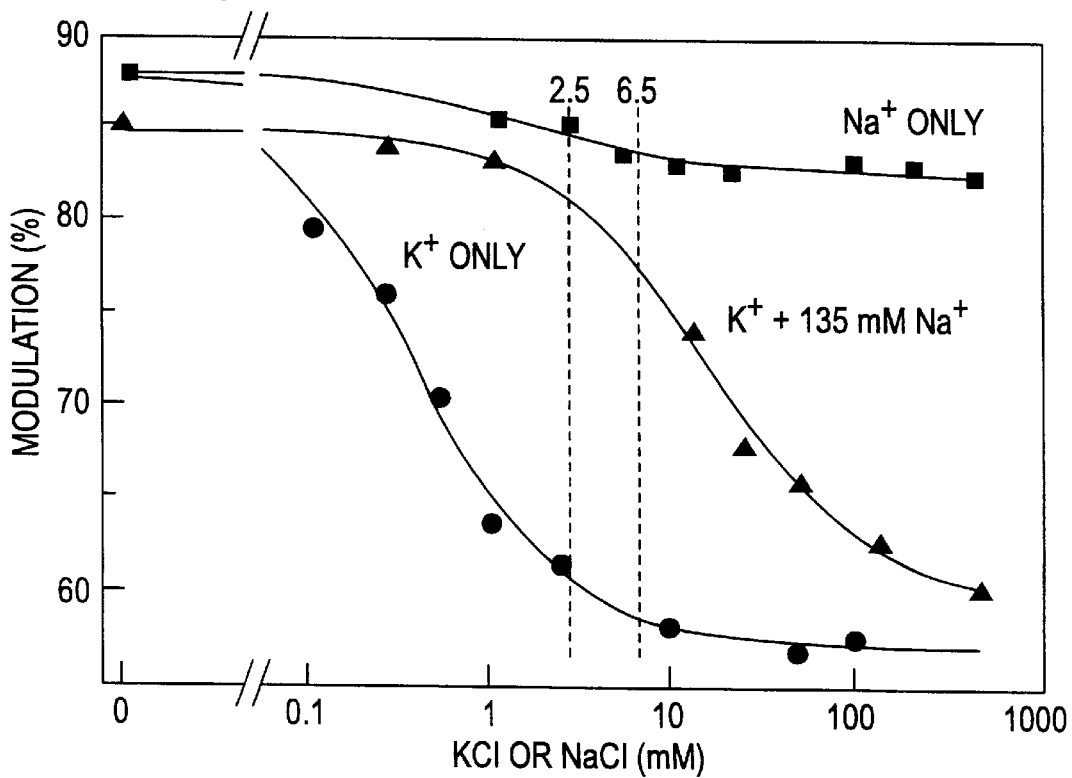

The usefulness of phase and modulation sensing for measuring $K^+$ is shown in FIG. 9, where potassium dependent changes in phase and lifetime are observed even in the presence of 135 mM of sodium. Data at the modulation frequency of 286 MHZ was used to determine the $K^+$-dependent phase angles and modulations at presence of 135 mM of $Na^+$. The choice of modulation frequency of 286 MHZ is of course arbitrary. A frequency higher than 500 MHZ could be chosen, but this may require a faster detector than standard photomultiplier tube (PMT), such as a microchannel plate PMT which is an expensive device, or a photodiode which is typically less sensitive.

Another unexpected feature of the CD 222, which makes this probe particularly useful for measuring $K^+$ concentrations in the presence of high concentrations of $Na^+$, is that the presence of $Na^+$ causes a shift in the $K^+$ sensitive range to higher concentrations. This is due to the competitive binding of sodium to the CD 222. FIG. 9 shows that the modulation is dependent on the $K^+$ concentration in the physiological range in the presence of 135 mM of $Na^+$.

The phase angles and modulations of CD 222 display good sensitivity to $K^+$ and only modest sensitivity to $Na^+$ (FIG. 9). The apparent dissociation constants from the phase angles are 0.54 mM for $K^+$ and 1.74 mM for $Na^+$, and 0.35 mM for $K^+$ and 1.3 mM for $Na^+$ from the modulation data. More important are changes in the phase angle and modulation in the presence of both the cations. These changes are 32.4 degrees in phase and 29.8% in modulation for $K^+$ binding, and only of 3.4 degrees and 4.9% for $Na^+$ binding to the CD 222 at 286 MHz. The $K^+$ induced changes in the phase angle and modulation are excellent for measurements of $K^+$, particularly at frequencies higher than 200 MHz. The dynamic range for $K^+$ is somewhat decreased by the presence of sodium, but the range of phase and modulation values is still adequate for lifetime-based sensing of $K^+$.

These phase and modulation data indicate that $Na^+$ binding does not cause a significant change in the lifetime of CD 222. This is an important observation because almost the entire dynamic range in the phase and modulation remains available for $K^+$ sensing. However, the presence of sodium in the solution has a large impact on binding of $K^+$. The $K^+$-sensitive range is dramatically shifted toward higher $K^+$ concentration in the presence of 135 mM $Na^+$, resulting in apparent dissociation constants for $K^+$ of 34.2 mM and 15.5 mM from phase and modulation, respectively. This means that the apparent binding affinity for $K^+$ decreased 63-fold from phase angle and 44-fold from modulation. In spite of decrease of $K^+$ affinity, the phase angle and modulation data for CD 222 are promising parameters for $K^+$ sensing in the blood. Measurements with an accuracy of 0.12 degree in phase and 0.2% in modulation are sufficient to fulfill the required tolerance of 0.2 mM in the range from 2.5 to 6.5 mM of $K^+$ concentration. Such accuracy for phase and modulation measurements can be obtained with commercial frequency-domain instruments. The accuracy can be improved if excitation wavelengths shorter than 380 nm are used.

What is claimed is:

1. A method of optically measuring $Na^+$ concentration in a sample containing $Na^+$ at a concentration of above 100 mM and up to 160 mM, the sample further containing a concentration of 2.5–6.5 mM of $K^+$, said method comprising the steps of:

adding to a sample containing an ionic solute of $Na^+$ a photoluminescent ligand probe capable of measuring concentration of $Na^+$ in the sample containing $Na^+$ at a concentration of above 100 mM and up to 160 mM, the sample further containing a concentration of 2.5–6.5 mM of $K^+$, wherein said probe is non-covalently bound to the ionic solute of sodium to form a sodium-bound probe species, and wherein bound and unbound species of said probe exist in said sample, said probe having intrinsic sodium-induced lifetime changes;

exciting said sample with radiation;

detecting the resulting emission beam from said bound and unbound species; and performing a calculation utilizing the apparent luminescence lifetime of the emission to determine the $Na^+$ concentration of said sample without utilizing fluorescence intensity in said calculation to determine the sodium concentration; wherein said sample is selected from the group consisting of blood and serum.

2. A method as in claim 1, wherein said probe is a fluorescent probe.

3. A method as in claim 1, wherein the lifetime is calculated using phase-modulation fluorometry.

4. A method as in claim 1, further comprising the step of changing the apparent concentration sensitivity range of the probe by changing the wavelength of the modulated excitation and/or the wavelength of the emission.

5. A method as in claim 1, wherein the lifetime is calculated using time-resolved fluorometry.

6. A method as in claim 1, wherein the sample is excited using frequency-doubled output of pyridine 2 dye laser.

7. A method as in claim 1, wherein the sample is excited using frequency-doubled Ti:sapphire laser.

8. A method as in claim 1, wherein said probe is sodium binding benzofuran oxazole ("SBFO").

9. A method of optically measuring $K^+$ concentration in a sample containing an ionic solute of $K^+$ at a concentration of 2.5–6.5 mM, with $Na^+$ present in a concentration of above 100 mM and up to 160 mM, said method comprising the steps of:

adding a coumarin diacid cryptant ("CD 222") probe to a sample to be analyzed, said sample containing $K^+$ in an ionic solute at a concentration of 2.5–6.5 mM, and having $Na^+$ present in a concentration of above 100 mM and up to 160 mM, wherein said probe is non-covalently bound to an ionic solute of $K^+$ to form a $K^+$-bound probe species, and wherein bound and unbound species of said probe exist in said sample;

exciting the sample with radiation;

detecting the resulting emission beam from said bound and unbound species; and performing a calculation utilizing the apparent luminescence lifetime of the emission to determine the potassium concentration of the sample without utilizing fluorescence intensity in said calculation to determine the potassium concentration; wherein said sample is selected from the group consisting of blood and serum.

10. A method as in claim 9, wherein the lifetime is calculated using phase-modulation fluorometry.

11. A method as in claim 9, further comprising the step of changing the apparent concentration sensitivity range of the CD222 probe by changing the wavelength of the modulated excitation and/or the wavelength of the emission.

12. A method as in claim 9, wherein the lifetime is calculated using time-modulation fluorometry.

13. A method as in claim 9, wherein the sample is excited using frequency-doubled pyridine 2 dye laser.

14. A method as in claim 9, wherein the sample is excited using frequency-doubled Ti:sapphire laser.

* * * * *